US010126194B2

(12) United States Patent
Lee

(10) Patent No.: US 10,126,194 B2
(45) Date of Patent: Nov. 13, 2018

(54) SUBSCRIBER IDENTITY MODULE RECOGNITION METHOD UTILIZING AIR PRESSURE AND ELECTRONIC DEVICE PERFORMING THEREOF

(71) Applicant: Samsung Electronics Co., Ltd., Gyeonggi-do (KR)

(72) Inventor: Gwang Hui Lee, Gyeongsangbuk-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 258 days.

(21) Appl. No.: 15/079,461

(22) Filed: Mar. 24, 2016

(65) Prior Publication Data

US 2016/0282113 A1 Sep. 29, 2016

(30) Foreign Application Priority Data

Mar. 25, 2015 (KR) ........................ 10-2015-0041430

(51) Int. Cl.

| | |
|---|---|
| ***G01L 19/00*** | (2006.01) |
| ***G06F 1/32*** | (2006.01) |
| ***A61B 5/021*** | (2006.01) |
| ***A61B 5/00*** | (2006.01) |
| ***G04G 21/02*** | (2010.01) |
| ***G06F 1/16*** | (2006.01) |

(52) U.S. Cl.

CPC .............. *G01L 19/00* (2013.01); *A61B 5/021* (2013.01); *A61B 5/681* (2013.01); *G04G 21/02* (2013.01); *G06F 1/1656* (2013.01); *G06F 1/1684* (2013.01); *G06F 1/3293* (2013.01); *A61B 2560/029* (2013.01)

(58) Field of Classification Search

CPC ........... G01L 19/149; G01L 2019/0053; G01L 19/086; G01L 13/00; G01L 13/02–13/028; G01L 13/06; A61B 2560/029; A61B 5/681

USPC .............. 73/384–387, 863; 702/140, 94, 98; 713/323

See application file for complete search history.

(56) References Cited

U.S. PATENT DOCUMENTS 9,048,594 B2 6/2015 Lim et al.
2005/0252300 A1* 11/2005 Miller .................. G01L 9/0058 73/715

(Continued)

FOREIGN PATENT DOCUMENTS

CN 103108062 A * 5/2013

OTHER PUBLICATIONS

Machine Translation of CN103108062.*

*Primary Examiner* — Daniel S Larkin
*Assistant Examiner* — David L Singer
(74) *Attorney, Agent, or Firm* — Cha & Reiter, LLC

(57) ABSTRACT

A method for determining whether a module is mounted and an electronic device performing the same are provided. The electronic device includes a pressure sensor configured to detect barometric pressure inside the electronic device, a module mounting structure configured to mount a module, and a processor configured to determine whether or not the module is mounted in the module mounting structure, based on the variation in the detected pressure. In an embodiment, the pressure sensor is a barometric pressure sensor that detects variations in barometric pressure.

18 Claims, 10 Drawing Sheets

(56) References Cited

U.S. PATENT DOCUMENTS

| | | | | |
|---|---|---|---|---|
| 2009/0259865 | A1* | 10/2009 | Sheynblat | G06F 1/3203 713/323 |
| 2010/0286817 | A1* | 11/2010 | Goeking | A47K 10/26 700/231 |
| 2010/0313050 | A1* | 12/2010 | Harrat | G06F 1/3203 713/323 |
| 2012/0009979 | A1* | 1/2012 | Thill | H04W 4/70 455/558 |
| 2013/0109415 | A1* | 5/2013 | Seo | H04W 52/0251 455/458 |
| 2013/0325385 | A1* | 12/2013 | Shin | G01C 5/06 702/94 |
| 2014/0013141 | A1* | 1/2014 | Heo | G06F 1/3293 713/323 |
| 2014/0113495 | A1 | 4/2014 | Lim et al. | |
| 2015/0328081 | A1* | 11/2015 | Goldenberg | A61H 23/02 600/38 |
| 2015/0350393 | A1* | 12/2015 | Midori | H04M 1/18 455/575.8 |

* cited by examiner

SUBSCRIBER IDENTITY MODULE RECOGNITION METHOD UTILIZING AIR PRESSURE AND ELECTRONIC DEVICE PERFORMING THEREOF

CLAIM OF PRIORITY

This application claims the benefit of priority under 35 U.S.C. § 119(a) from a Korean patent application filed on Mar. 25, 2015 in the Korean Intellectual Property Office and assigned Serial number 10-2015-0041430, the entire disclosure of which is hereby incorporated by reference.

BACKGROUND

Field of the Disclosure

The present disclosure relates to a method for recognizing a module which is mounted and an electronic device performing thereof.

Description of the Related Art

In recent years, an electronic device is implemented with a smartphone which a user is able to carry, or with a form of wearable device that is attachable to a portion of a user's body. Research and development of high-functional electronic devices are forwarded energetically with the development of the mobile communication technology, and thus the electronic device is able to provide a user with various functions which were not available before.

To further provide various functions to a user, an electronic device may include an interface which is able to mount an external hardware (e.g., a circuit configuration, a module, or the like). This interface may allow the electronic device to secure external expandability.

In addition, the electronic device is able to provide a user with the convenience of the portability. For example, in the case where an electronic device is embodied as a wearable device, the electronic device does not obstruct movement of the user's body. Therefore, development of such devices strive to achieve weight reduction, slimming, and miniaturization in addition to high functionality are required with respect to the electronic devices.

SUMMARY

Aspects of the present disclosure address at least some of the above-mentioned problems and/or disadvantages and to provide at least some of the advantages described below. Accordingly, one of the aspects of the present disclosure is to provide a method for determining whether a module is mounted, based on a variation in the barometric pressure inside the electronic device due to module mounting and an electronic device performing the same.

In accordance with an aspect of the present disclosure, an electronic device may include a barometric pressure sensor configured to detect a barometric pressure inside the electronic device, a module mounting structure configured to mount a module, and at least one processor configured to determine whether the module is mounted in the module mounting structure, based on the variation in the detected barometric pressure.

Other aspects, advantages, and salient features of the disclosure will become apparent to those skilled in the art by reading the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
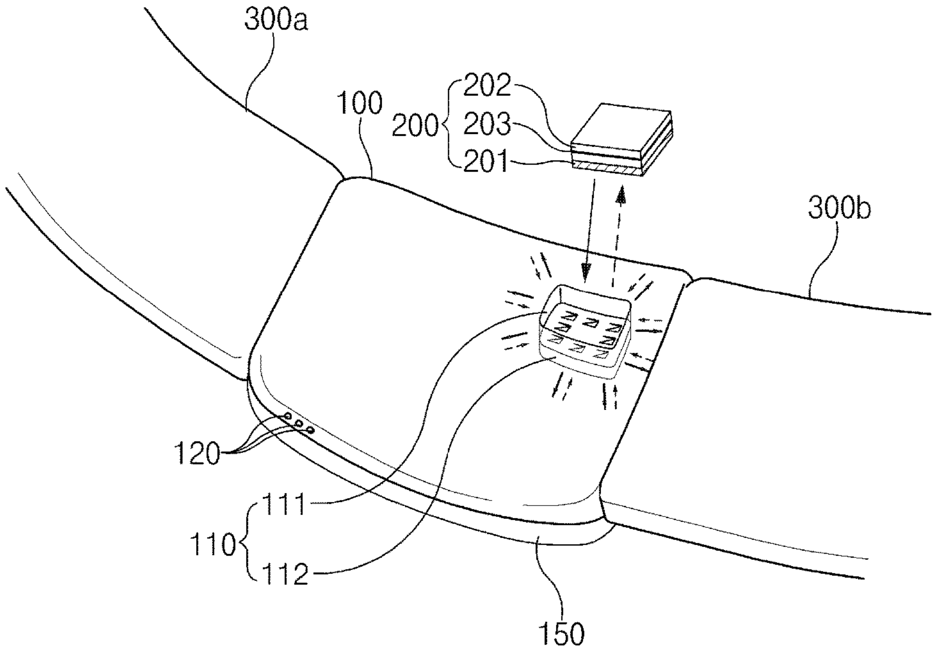
FIG. 1 is a diagram illustrating one example of an environment in which various embodiments of the present disclosure are applied.

Various embodiments of the present disclosure are described with reference to accompanying drawings. Accordingly, those of ordinary skill in the art will recognize that modifications, equivalent arrangements, and/or alternative constructions of the various embodiments described herein can be made without departing from the scope and spirit of the present disclosure. With regard to description of drawings, similar components may be identified with similar reference numerals.

In the disclosure disclosed herein, expressions such as "have", "may have", "include" and "comprise", or "may include" and "may comprise" as used herein indicate existence of corresponding features (e.g., elements such as numeric values, functions, operations, or components) but do not exclude presence of additional features.

In the disclosure disclosed herein, the expressions "A or B", "at least one of A or/and B", or "one or more of A or/and B", and the like used herein may include any and all combinations of one or more of the associated listed items. For example, the term "A or B", "at least one of A and B", or "at least one of A or B" may refer to all of: the case (1) where at least one A is included, the case (2) where at least one B is included, or the case (3) where both of at least one A and at least one B are included.

The terms, such as “first”, “second”, and the like used herein may refer to various elements of various embodiments of the present disclosure, but do not limit the elements. For example, such terms do not limit the order and/or priority of the elements. Furthermore, such terms may be used to distinguish one element from another element. For example, “a first user device” and “a second user device” indicate different user devices and does not imply order. For example, without departing the scope of the present disclosure, a first element may be referred to as a second element, and similarly, a second element may be referred to as a first element.

It will be understood that when an element (e.g., a first element) is referred to as being “operatively or communicatively” “coupled with/to”, or “connected to” another element (e.g., a second element), the first element can be directly coupled with/to or connected to the other element or an intervening element (e.g., a third element) may be present. In contrast, when an element (e.g., a first element) is referred to as being “directly coupled with/to” or “directly connected to” another element (e.g., a second element), it should be understood that there are no intervening element(s) (e.g., a third element).

Terms in this specification are used to describe specified embodiments of the present disclosure and are not intended to limit the scope of the present disclosure. Moreover, the terms of a singular form may include plural forms unless otherwise specified. Unless otherwise defined herein, all the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal detect unless expressly so defined herein in various embodiments of the present disclosure. In some cases, even if terms are defined in the specification, they may not be interpreted to exclude embodiments of the present disclosure.

An electronic device according to various embodiments of the present disclosure may include at least one of smartphones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, mobile medical devices, cameras, or wearable devices. According to various embodiments of the present disclosure, the wearable device may include at least one of an accessory type (e.g., watch, ring, bracelet, ankle bracelet, necklace, glasses, contact lens, or head-mounted-device (HMD)), a fabric or clothing type (e.g., electronic apparel), a physical attachment type (e.g., skin pad or tattoo), or a body implantation type (e.g., implantable circuit).

According to an aspect of the disclosure, the electronic device may be embodied as a home appliance. The smart home appliances may include at least one of, for example, televisions (TVs), digital versatile disc (DVD) players, audios, refrigerators, air conditioners, cleaners, ovens, microwave ovens, washing machines, air cleaners, set-top boxes, TV boxes (e.g., Samsung HomeSync™, Apple TV™, or Google game consoles (e.g., Xbox™ and PlayStation™), electronic dictionaries, electronic keys, camcorders, electronic picture frames, and the like.

According to various embodiments of the present disclosure, the electronic devices may include at least one of medical devices (e.g., various portable medical measurement devices (e.g., a blood glucose monitoring device, a heartbeat measuring device, a blood pressure measuring device, a body temperature measuring device, and the like)), a magnetic resonance angiography (MRA), a magnetic resonance imaging (MRI), a computed tomography (CT), scanners, and ultrasonic devices) receiving a user input in an idle mode, navigation devices, global positioning system (GPS) receivers, event data recorders (EDRs), flight data recorders (FDRs), vehicle infotainment devices, electronic equipment for vessels (e.g., navigation systems and gyrocompasses), avionics, security devices, head units for vehicles, industrial or home robots, automatic teller's machines (ATMs), points of sales (POSs), or internet of things (e.g., light bulbs, various sensors, electric or gas meters, sprinkler devices, fire alarms, thermostats, street lamps, toasters, exercise equipment, hot water tanks, heaters, boilers, and the like).

According to various embodiments of the present disclosure, the electronic devices may include at least one of parts of furniture or buildings/structures, electronic boards, electronic signature receiving devices, projectors, or various measuring instruments (e.g., water meters, electricity meters, gas meters, or wave meters, and the like). According to various embodiments, the electronic device may be one of the above-described devices or a combination thereof. An electronic device according to an embodiment may be a flexible electronic device. Furthermore, an electronic device according to an embodiment may not be limited to the above-described electronic devices and may include other electronic devices and new electronic devices according to the development of technologies.

Hereinafter, electronic devices according to an embodiment of the present disclosure will be described with reference to the accompanying drawings. The term “user” used herein may refer to a person who uses an electronic device or may refer to a device (e.g., an artificial electronic device) that uses an electronic device.

Furthermore, an electronic device according to various embodiments may be a watch-type wearable device (so-called, a smart watch). However, the scope and spirit of the present disclosure may not be limited thereto.

FIG. 1 is a diagram illustrating an environment in which various embodiments of the present disclosure are applied.

Referring now to FIG. 1, an environment in which various embodiments of the present disclosure are applied may include an electronic device 100, a module 200 which is to be mounted in the electronic device 100, and bands 300*a* and 300*b* which are coupled with the electronic device 100 to fasten the electronic device 100 to a user's wrist.

The electronic device 100 may include a module mounting structure 110, a ventilation hole 120, and a display 150. The display 150 may be implemented at one surface of the electronic device 100 and may provide an image based on various functions of the electronic device 100. The module mounting structure 110 may include a recessed portion 111, which is disposed at a portion of the other surface of the electronic device 100 and enables a mechanical coupling with the module 200, and a module coupling portion 112 which is disposed at a bottom of the recessed portion 111 and enables an electrical coupling with the module 200. The module coupling portion 112 may include several protrusions, and the several protrusions may be electrically coupled with a contact portion 201 of the module 200. The internal and external air of the electronic device 100 may pass through the ventilation hole 120. For example, the ventilation hole 120 may be covered with a gas permeable material (e.g., Goretex™) which allows gas to pass through the ventilation hole 120 and is able to repel liquid.

According to an embodiment of the present disclosure, it may be understood that the module 200 is implemented with a hardware component which includes one or more circuits. For example, the module 200 may include the contact portion 201, a module housing 202, and a rubber packing 203. The contact portion 201 may be a component which enables electrical coupling between the module 200 and the electronic device 100 and may make contact with the module coupling portion 112 of the electronic device 100. The contact portion 201 may be mountable or removable in or from the module 200. Furthermore, the contact portion 201 itself may be used as the module 200 or may be used as an independent circuit (e.g., an integrated circuit (IC) chip). The module housing 202 may be coupled with the contact portion 201 and may have a shape corresponding to a shape of the recessed portion 111 of the electronic device 100. Furthermore, the module housing 202 may include a circuitry which includes the contact portion 201 as a portion thereof. The rubber packing 203 may be formed around the module housing 202. The electronic device 100 in which the module 200 is mounted may achieve a waterproof function with the rubber packing 203.

Figure 2:
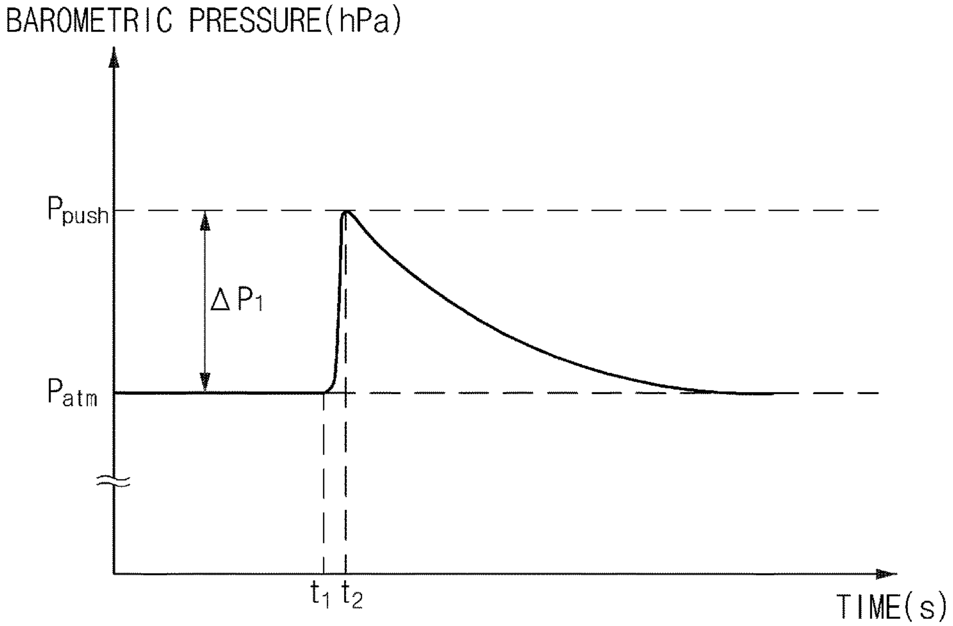
FIG. 2 is a graph illustrating changes in barometric pressure versus tune inside an electronic device when a module is mounted therein, according to an embodiment of the present disclosure.

FIG. 2 is a graph illustrating a changes in barometric pressure inside an electronic device when a module is mounted therein, according to an embodiment of the present disclosure.

FIG. 2 shows a graph which indicates barometric pressure inside the electronic device 100 according to an embodiment of the present disclosure. For example, in the case where the module 200 is not mounted in the electronic device 100, the barometric pressure inside the electronic device 100 may maintain the balance with the external atmospheric pressure through the recessed portion 111 and/or the ventilation hole(s) 120. For example, before the module 200 is mounted in the electronic device 100, a value of the barometric pressure inside the electronic device 100 may be the same as that of the external atmospheric pressure Patm (e.g., 1 atm=1013.25 hPa).

While the barometric pressure inside the electronic device 100 maintains the balance with the external atmospheric pressure, if the module 200 is coupled and mounted in the electronic device 100 at t1, some of the air may be compressed in the direction of the inside of the electronic device 100 as much as a volume of the recessed portion 111 of the electronic device 100. At this time, since the ventilation hole 120 is covered with the Goretex™ material, the barometric pressure inside the electronic device 100 may temporarily increase. For example, the barometric pressure inside the electronic device 100 may increase due to the mounting of the module 200 by $\Delta$P1 and may have a value of Ppush (=Patm+$\Delta$P1) at t2. For example, if the value of $\Delta$P1 is 12 hPa, the value of Ppush will be 1025.25 hPa.

Since the electronic device 100 has the ventilation hole 120, the barometric pressure inside the electronic device 100 may gradually begin to decrease at t2 and as shown the barometric pressure inside the electronic device may balance with the external atmospheric pressure again.

Figure 3:
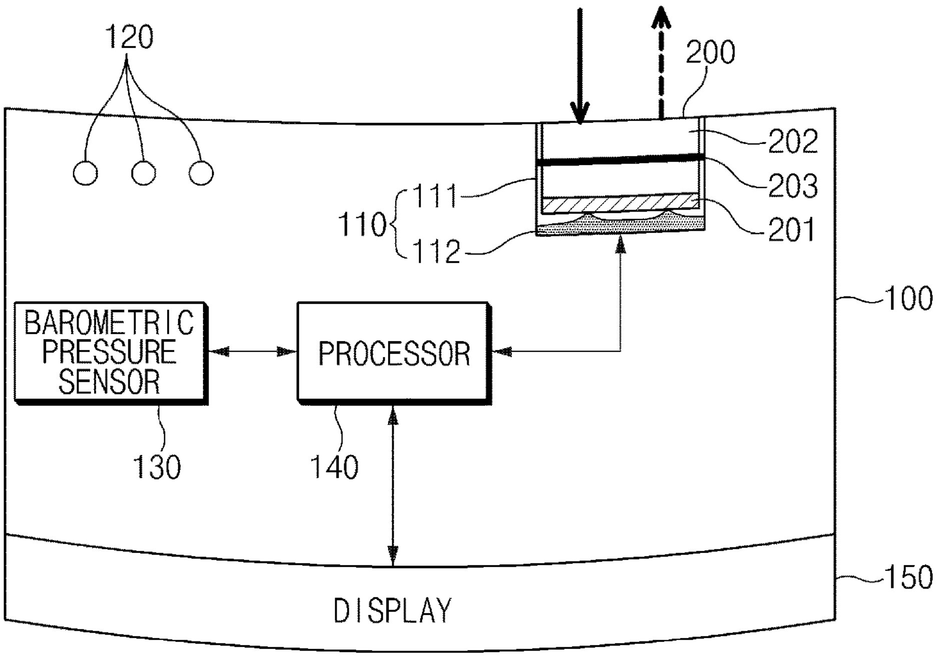
FIG. 3 is a block diagram illustrating a configuration of an electronic device according to an embodiment of the present disclosure.

FIG. 3 is a block diagram illustrating a configuration of an electronic device according to an embodiment of the present disclosure.

Referring now to FIG. 3, the electronic device 100 according to an embodiment of the present disclosure may include the module mounting structure 110, the ventilation hole(s) 120, a barometric pressure sensor 130, at least one processor 140, and the display 150. According to an embodiment, the barometric pressure sensor 130 may be referred to as a barometer sensor, atmospheric pressure sensor, or simply a pressure sensor. However, it is within the spirit and scope of the disclosure, and the appended claims, that a pressure sensor with a diaphragm could also be used. According to an embodiment, the electronic device 100 may not include at least one of the above-described components or may further include other component(s). Meanwhile, in FIG. 3, descriptions about components denoted by the same reference numerals with regard to FIG. 1 will be omitted.

The module 200 may be mounted, for example, in the module mounting structure 110. For example, the module mounting structure 110 may include the recessed portion 111 which enables a mechanical coupling with the module 200 and the module coupling portion 112 which enables an electrical coupling with the module 200.

The internal and external air of the electronic device 100 may pass through the ventilation hole(s) 120. For example, the ventilation hole 120 may be covered with a permeable material (e.g., Goretex™) which allows gas to pass through the ventilation hole(s) 120 and is able to repel liquid.

The barometric pressure sensor 130 detects barometric pressure, for example, inside the electronic device 100. Since the external air passes through the ventilation hole(s) 120 of the electronic device 100, generally, the barometric pressure inside the electronic device 100 may be the same as the external atmospheric pressure. However, as illustrated in FIG. 2, in the case where the module 200 is mounted in the module mounting structure 110, the barometric pressure inside the electronic device 100 may temporarily change (e.g., increase) until the pressure balance is achieved through the ventilation hole(s) 120. Typically, the mounting of the module 200 will compress some of the air at least temporarily, thus causing an increase in pressure detected by the barometric pressure sensor 130.

Based on the variation in the barometric pressure detected by the barometric pressure sensor 130, the processor 140 may determine whether the module 200 has been mounted or not in the module mounting structure 110. For example, in the case where the variation in the barometric pressure detected by the barometric pressure sensor 130 is greater than or equal to a specific value, the processor 140 may be configured to determine whether the module 200 is mounted or not (whether or not of mounting or removal).

In general, since the atmospheric pressure gradually changes according to a weather change on a daily basis (e.g., around 4 hPa in 24 hours, that is, around 0.17 hPa in an hour), the atmospheric pressure may be almost constant during several minutes or seconds. Therefore, the processor 140 may distinguish the change in the barometric pressure due to the mounting of the module 200 from the change in the atmospheric pressure.

According to an embodiment of the present disclosure, if the variation in the barometric pressure detected by the barometric pressure sensor 130 is greater than or equal to a specific value (e.g., 7 hPa) during a specific period of time (e.g., several seconds), the processor 140 may be configured to determine whether the module 200 is mounted or not. According to another embodiment, the processor 140 may be configured to determine whether the module 200 is mounted or not, based on the instantaneous change rate (hPa/sec) of the barometric pressure detected by the barometric pressure sensor 130.

According to an embodiment of the present disclosure, in order to determine whether the module 200 is mounted or not, the processor 140 may transmit a module search signal to the module mounting structure 110. The processor 140 may determine whether the module 200 is mounted or not, based on whether a response signal of the module search signal is received (e.g., polling).

For example, if the response signal of the module search signal is received, the processor 140 may determine that the module 200 is mounted in the module mounting structure 110. In contrast, if the response signal is not received during a specific period of time, the processor 140 may re-transmit the module search signal to the module mounting structure 110. However, since the processor 140 is able to transmit the module search signal to the module mounting structure 110, in which the module 200 is not mounted, without restriction, the number of times that the module search signal is transmitted may be set in advance. For example, if the response signal is not received even though the module search signal is transmitted as a specific time period, the processor 140 may determine that the module 200 is removed from the module mounting structure 110.

Meanwhile, the processor 140 may transmit the module search signal to various circuit components connected directly and indirectly to the processor 140 as well as the module mounting structure 110. For example, the processor 140 may determine that the display 150 is mounted in the electronic device 100, by transmitting the module search signal to the display 150 (or a driving circuit of the display 150) and receiving the corresponding response signal. According to an embodiment of the present disclosure, the processor 140 may determine whether the module 200 is mounted, based on not whether the response signal is received but substantive content of the received response signal. Furthermore, according to an embodiment of the present disclosure, the response signal may include information for distinguishing a module or a circuit component which transmitted the response signal.

Figure 4:
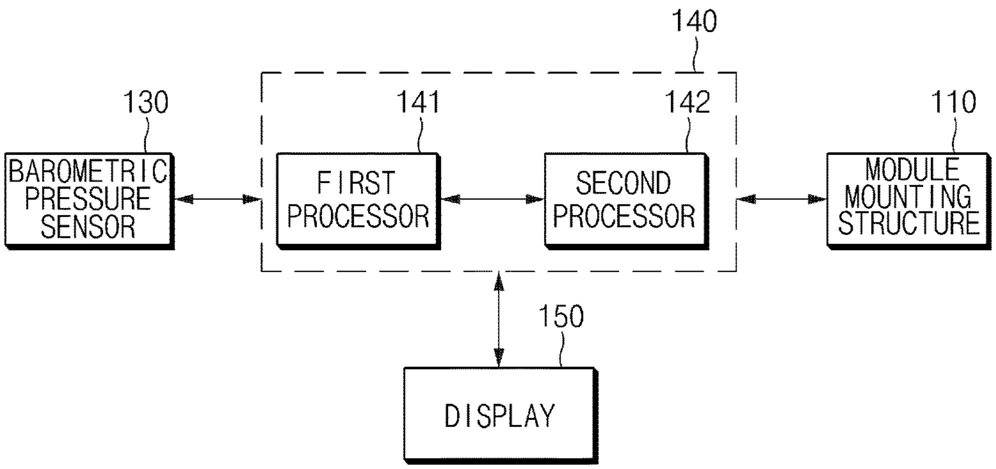
FIG. 4 is a block diagram of at least one processor which includes a low-power processor, according to an embodiment of the present disclosure.

FIG. 4 is a block diagram of at least one processor which includes a low-power processor, according to an embodiment of the present disclosure.

Referring now to FIG. 4, the at least one processor 140 according to an embodiment of the present disclosure may include a first processor 141 and a second processor 142. The processors do not constitute pure software or software per se, and include, for example, circuitry such as an integrated circuit.

The first processor 141 may be a low-power processor which consumes less power than the second processor 142 during an operation. For example, the first processor 141 may be implemented with a microcontroller unit (MCU) which consumes less power than the second processor 142. Even though the second processor 142 is in a sleep state (or a doze state), the first processor 141 may be independently driven at all times. The first processor 141 may receive electrical signals transmitted from various sensors including the barometric pressure sensor 130. Accordingly, as of a result of its ability to receive signals from various sensors, the first processor 141 may be referred to as "sensor hub".

According to an embodiment of the present disclosure, if the variation in the barometric pressure detected by the barometric pressure sensor 130 is greater than or equal to a specific value, the first processor 141 may generate an interrupt and may transmit the generated interrupt to the second processor 142. The interrupt may refer to an interrupt which requests the processor 142 to determine whether the module 200 is mounted or not.

The second processor 142 may perform all or a part of functions of the processor 140 illustrated in FIG. 3. For example, the second processor 142 may be implemented with an application processor (AP). The second processor 142 may perform a specific operation in an active state. However, in the case where the second processor 142 does not perform the specific operation, the second processor 142 may switch from the active state to a sleep state, thereby reducing the power consumption.

According to an embodiment of the present disclosure, upon receiving an interrupt from the first processor 141, the second processor 142 may be configured to switch from the sleep state to the active state. If receiving the interrupt, the second processor 142 may transmit a module search signal to the module mounting structure 110. The second processor 142 may determine whether the module is mounted or not, based on whether a response signal corresponding to the module search signal is received.

Returning now to FIG. 3, under control of the processor 140, the display 150 may provide an image according to various functions of the electronic device 100. For example, the display 150 may correspond to a flexible display illustrated in FIGS. 1 and 3.

The module 200 is a statutory element that comprises a unit of hardware which is mountable or removable in or from the electronic device 100, or a unit which is a combination of the hardware and software or firmware. The module 200 may be implemented mechanically and/or electronically.

For example, the module 200 may include a camera module such as a CCD or CMOS, a storage module (e.g., an external memory), various sensor modules (e.g., a heartbeat sensor module, an illuminance sensor module, an acceleration sensor module, a temperature sensor module, and the like), a display module (e.g., the display 150), a user interface module (e.g., a physical button), a speaker module, a microphone module, a communication module, and an additional processor module, just to name some non-limiting possibilities. In addition, the module 200 may include at least one of an application-specific integrated circuit (ASIC) chip, field-programmable gate arrays (FPGAs), or a programmable-logic device, which performs some operations and are known or will be developed.

With reference to FIG. 3, according to an embodiment of the present disclosure, the module 200 may include the contact portion 210, the module housing 202, and the rubber packing 203. The module 200 may be electrically coupled with the electronic device 100 through the contact portion 201.

The contact portion 201 may make contact with the module coupling portion 112 of the module mounting structure 110, and thus the electrical connection between the electronic device 100 and the module 200 may be implemented. The contact portion 201 may implement an independent circuit by itself. For example, the contact portion 201 itself may correspond to a subscriber identity module (SIM).

The module housing 202 may be coupled with the contact portion 201 and may have a shape corresponding to a shape of the recessed portion 111 of the electronic device 100. According to an embodiment of the present disclosure, the module housing 202 may include a circuit component (e.g., circuit components of the above-described various modules) which includes the contact portion 201 as a portion thereof.

With continued reference to FIG. 3, the rubber packing 203 may be formed around the module housing 202. For example, the rubber packing 203 may implement a waterproof function of the electronic device 100 together with Goretex™ material disposed in the ventilation hole 120.

Figure 5:
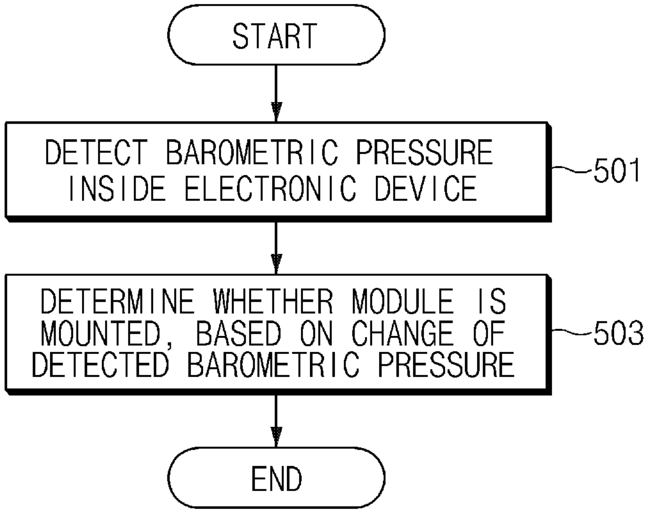
FIG. 5 is a flowchart illustrating an operational example of a module recognition method according to an embodiment of the present disclosure.

FIG. 5 is a simplified flowchart illustrating a module recognition method according to an embodiment of the present disclosure.

Referring now to FIG. 5, a module recognition method according to an embodiment of the present disclosure may include operation 501 and operation 503.

In operation 501, the electronic device 100 detects the barometric pressure inside the electronic device 100 through the barometric pressure sensor 130. In operation 503, the electronic device 100 may determine whether the module 200 corresponding to the module mounting structure 110 included in the electronic device 100 is mounted or not, based on a variation in the barometric pressure detected in operation 501.

Figure 6:
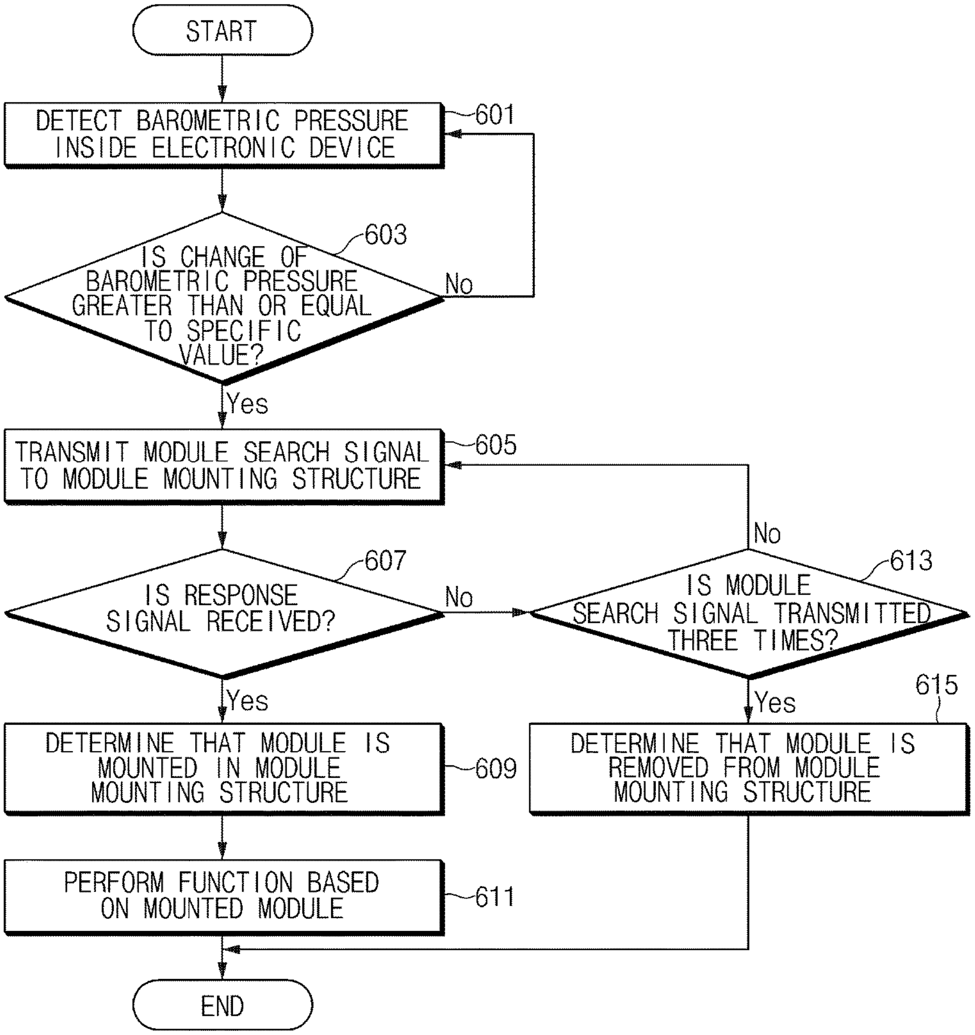
FIG. 6 is a flowchart illustrating an operational example of a module recognition method according to an embodiment of the present disclosure.

FIG. 6 is a flowchart illustrating an operational example of a module recognition method according to an embodiment of the present disclosure.

Referring now to FIG. 6, a module recognition method according to an embodiment of the present disclosure may include operations 601 to 615. For example, the module recognition method illustrated in FIG. 6 may be performed at the electronic device 100 illustrated in FIG. 3.

In operation 601, the barometric pressure sensor 130 of the electronic device 100 may detect the barometric pressure inside the electronic device 100. The barometric pressure sensor 130 may detect the barometric pressure inside the electronic device 100 in a specific time period or in real time. Information about the detected barometric pressure may be provided to the at least one processor 140.

In operation 603, the at least one processor 140 of the electronic device 100 may determine whether the variation in the barometric pressure detected in operation 601 is greater than or equal to a specific value. If the variation in the detected barometric pressure is greater than or equal to the specific value, the procedure proceeds to operation 605. Otherwise, the procedure returns to operation 601.

In operation 605, the at least one processor 140 of the electronic device 100 may transmit a module search signal to the module mounting structure 110 (see FIG. 3). According to an embodiment of the present disclosure, the at least one processor 140 of the electronic device 100 may transmit the module search signal to various circuit components connected to the at least one processor 140 as well as the module mounting structure 110.

In operation 607, the at least one processor 140 of the electronic device 100 may determine whether a response signal corresponding to the module search signal transmitted in operation 605 is received. For example, the at least one processor 140 of the electronic device 100 may determine whether the response signal corresponding to the module search signal is received in a specific period of time. According to an embodiment of the present disclosure, the at least one processor 140 may identify the module 200 or a circuit component, which transmitted the response signal, based on the response signal. If the response signal is received, the procedure proceeds to operation 609. Otherwise, the procedure proceeds to operation 613.

In operation 609, since the response signal corresponding to the module search signal is received, the at least one processor 140 of the electronic device 100 may determine that the corresponding module 200 is mounted in the module mounting structure 110.

In operation 611, the at least one processor 140 of the electronic device 100 may perform initialization about the module 200 determined as the mounted module. After the initialization is performed, the at least one processor 140 may perform a specific operation based on the module 200. After operation 611, the at least one processor 140 may end the module recognition method or may return to operation 601 (although not illustrated).

In operation 613, the processor 140 of the electronic device 100 may determine whether the module search signal is transmitted as many as a specific frequency. For example, the at least one processor 140 may determine whether the module search signal is transmitted three times. If the at least one processor 140 transmits the module search signal as many as the specific frequency, the procedure proceeds to operation 615. Otherwise, the procedure returns to operation 605.

In operation 615, since the response signal is not received even though the module search signal is transmitted to the module mounting structure 110 the specific frequency, the at least one processor 140 of the electronic device 100 may determine that the module 200 is released (that is, removed) from the module mounting structure 110. After operation 615, the at least one processor 140 may end the module recognition method or may return to operation 601 even though not illustrated.

Figure 7:
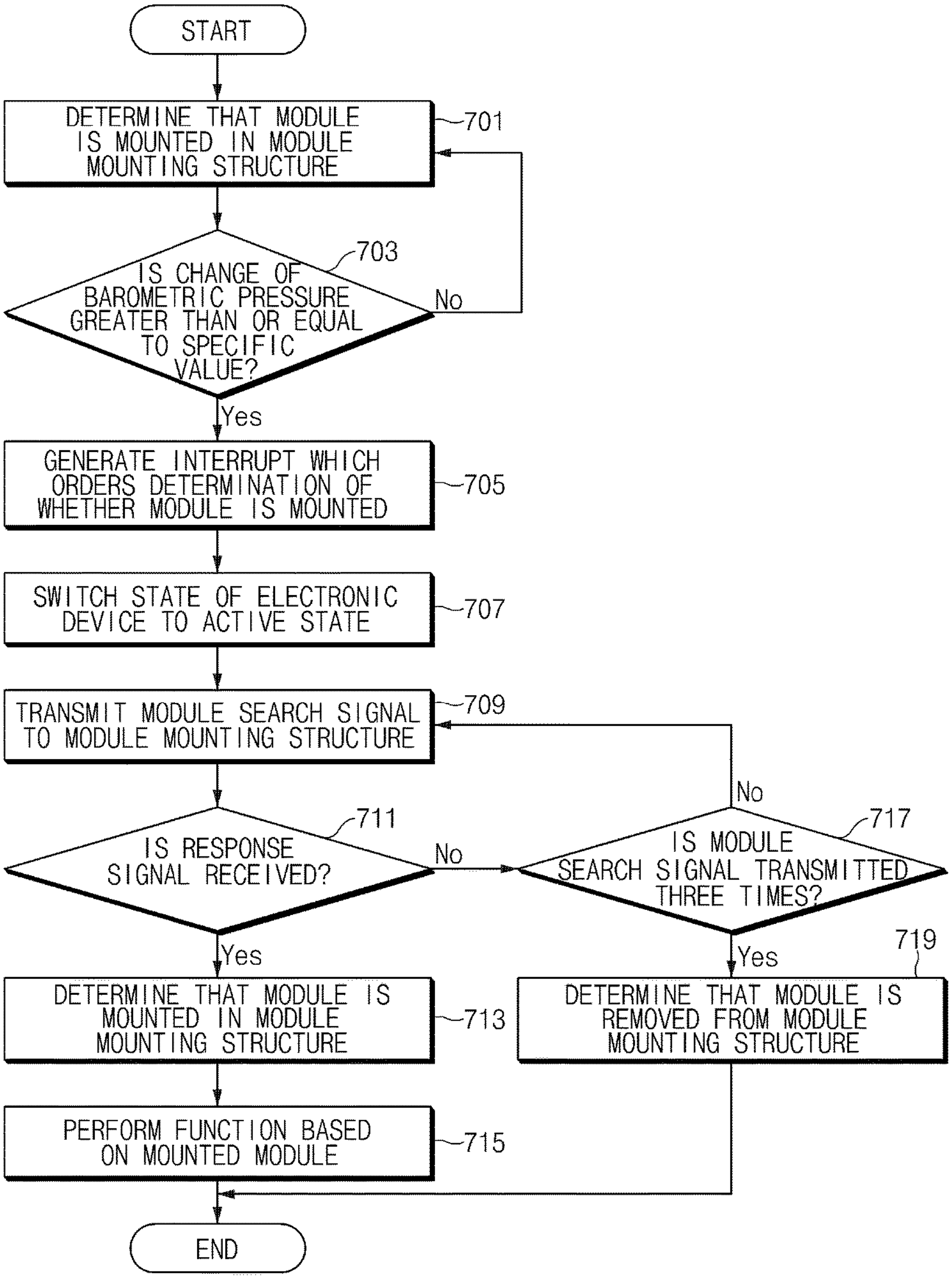
FIG. 7 is a flowchart illustrating an operational example of a module recognition method using a low-power processor, according to an embodiment of the present disclosure.

FIG. 7 is a flowchart illustrating a module recognition method using a low-power processor, according to an embodiment of the present disclosure.

Referring to FIG. 7, a module recognition method according to an embodiment of the present disclosure may include operation 701 to operation 719. Since operation 701 performed at the barometric pressure sensor 130 corresponds to operation 601 of FIG. 6, and operation 709 to operation 719 performed at the second processor 142 correspond to operation 605 to operation 615 of FIG. 6 performed at the processor 140, respectively, duplicated descriptions of corresponding operations will be omitted.

For example, the module recognition method illustrated in FIG. 7 may be performed at the electronic device 100 which includes the first and second processors 141 and 142 illustrated in FIG. 4.

In operation 703, the first processor 141 may determine whether the variation in the barometric pressure detected in operation 701 is greater than or equal to a specific value. If the variation in the detected barometric pressure is greater than or equal to the specific value, the procedure proceeds to operation 705. Otherwise, the procedure returns to operation 701.

In operation 705, the first processor 141 may generate an interrupt and may transmit the generated interrupt to the second processor 142. The interrupt may correspond to an interrupt which requests the second processor 142 to determine whether the module 200 is mounted or not.

In operation 707, the second processor 142 may be switched to an active state by the interrupt transmitted in operation 705. For example, if the second processor 142 is in a sleep state, the state of the second processor 142 may be switched to an active state. If the second processor 142 is already in an active state, the second processor 142 may maintain the active state.

A general electronic device may recognize various modules and/or circuit components included in the electronic device 100 when a state of the electronic device is switched from a power-off state to a power-on state and may use the various modules and/or circuit components based on the recognition.

However, if a specific module is mounted during an operation (that is, power-on state) of the general electronic device, it may be difficult whether the specific module is mounted. Accordingly, if the specific module is mounted in the general electronic device, to use the specific module, a user may essentially perform a rebooting, which turns off the power of the electronic device and then turns on the power of the electronic device.

On the other hand, according to various embodiments of the present disclosure, the electronic device 100 may determine whether the module 200 is mounted, based on the variation in the barometric pressure inside the electronic device 100 due to the mounting of the module 200. Accordingly, even though the module 200 is mounted during an operation of the electronic device 100, it may be instantly determined whether the module 200 is mounted. Therefore, according to various embodiments of the present disclosure, a user may not need a separate rebooting operation with respect to the electronic device 100.

In addition, the barometric pressure sensor 130 generally included in the electronic device 100 may be used in various embodiments of the present disclosure. Therefore, the electronic device 100 may not include a separate circuit component (e.g., a separate pin for searching a device and a transistor circuit corresponding to this) for recognizing the module 200, thereby making it possible to miniaturize and slim the electronic device 100.

Furthermore, according to various embodiments of the present disclosure, the electronic device 100 may include hardware a sensor hub (e.g., the low-power processor 141) implemented with MCU. The sensor hub may provide the variation in the barometric pressure detected by the barometric pressure sensor 130 to an AP (e.g., the processor 142), which is in a sleep state, using an interrupt. Accordingly, the electronic device 100 may instantly determine whether the module 200 is mounted or not, while consuming a very small amount of power.

According to an embodiment of the present disclosure, the module 200 may comprise a subscriber identity module (e.g., a universal subscriber identity module (USIM)) which is the basis of the telecommunication service charge. For example, a user may move a USIM from a first electronic device (e.g., a smart phone) to a second electronic device (e.g., a smart watch) and may mount the USIM on the second electronic device. At this time, the first and second electronic devices may be in a power-on state. Based on the variation in the barometric pressure due to the mounting of the USIM, the second electronic device may instantly recognize and use the USIM. In other words, according to an embodiment of the present disclosure, hot swapping the USIM between the first and second electronic devices which are in a power-on state may be implemented.

Furthermore, according to an embodiment, the electronic device 100 may be an electronic device on which a plurality of modules is mounted, and the plurality of modules may be implemented to be mounted or removed in or from the electronic device frequently. If an embodiment of the present disclosure is applied to the electronic device, the electronic device may recognize whether the plurality of modules is mounted or not, without a separate rebooting.

Figure 8:
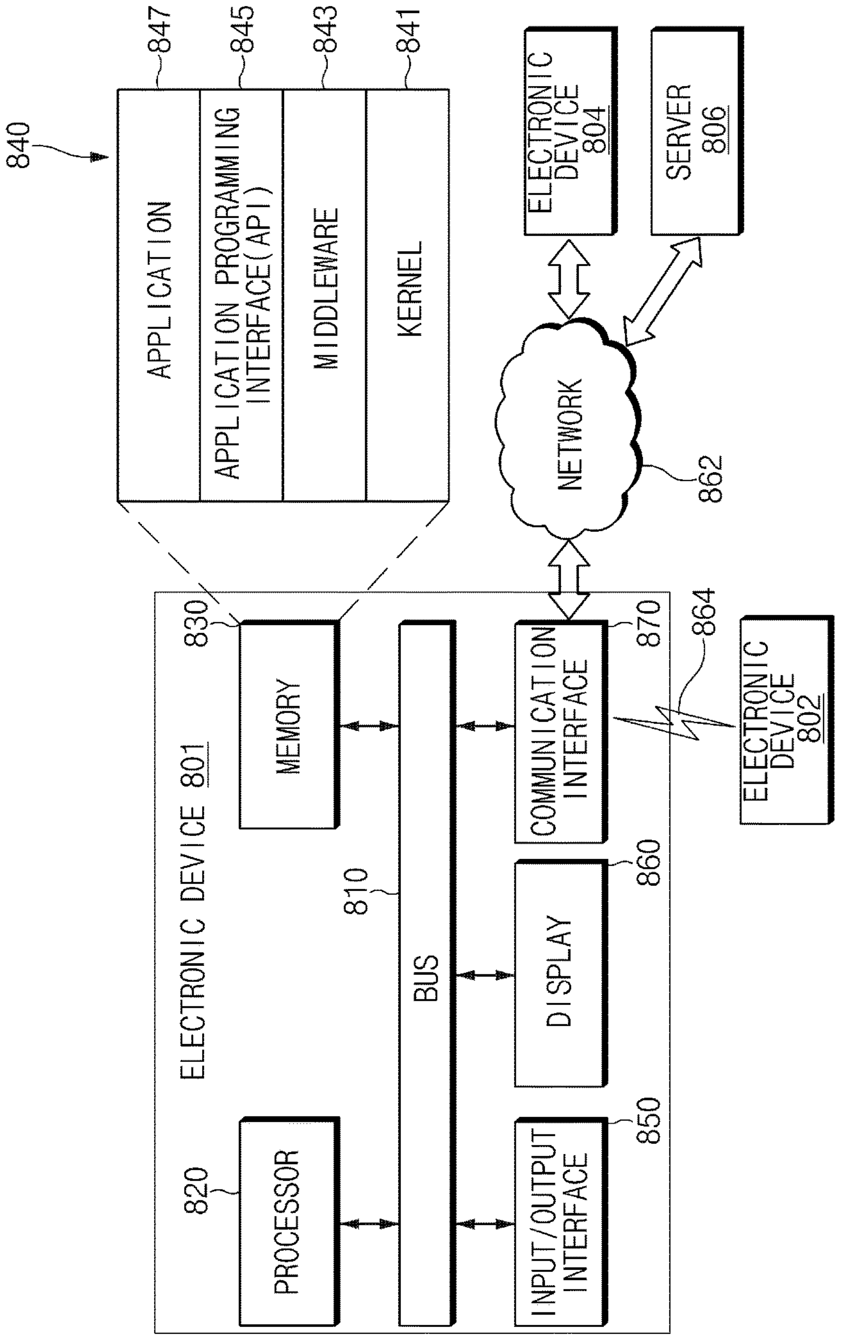
FIG. 8 is a block diagram illustrating a configuration of an electronic device according to various embodiments of the present disclosure.

FIG. 8 is a block diagram illustrating a configuration of an electronic device according to various embodiments of the present disclosure.

Referring to FIG. 8, there is illustrated an electronic device 801 in a network environment according to various embodiments of the present disclosure. For example, the electronic device 810 may correspond to the electronic device 100 illustrated in FIGS. 1 and 3. The electronic device 801 may include a bus 810, at least one processor 820, a memory 830, an input/output (I/O) interface 850, a display 860, and a communication interface 870. According to an embodiment, the electronic device 801 may not include at least one of the above-described components or may further include other component(s).

The bus 810 may interconnect the above-described components 820 to 870 and may be a circuit for conveying communications (e.g., a control message and/or data) among the above-described components.

The processor 820 may include one or more of a central processing unit (CPU), an application processor (AP), or a communication processor (CP). The processor 820 may correspond to the processor 140 of FIGS. 3 and 4. The processor 820 may perform, for example, data processing or an arithmetic operation associated with control or communication of at least one other component(s) of the electronic device 801.

With continued reference to FIG. 8, the memory 830 may include a volatile and/or nonvolatile memory. The memory 830 may store instructions or data associated with at least one other component(s) of the electronic device 801. According to an embodiment, the memory 830 may store software and/or a program 840. The program 840 may include, for example, a kernel 841, a middleware 843, an application programming interface (API) 845, and/or an application program (or an application) 847. At least a portion of the kernel 841, the middleware 843, or the API 845 may be called an "operating system (OS)".

The kernel 841 may control or manage system resources (e.g., the bus 810, the processor 820, the memory 830, and the like) that are used to execute operations or functions of other programs (e.g., the middleware 843, the API 845, and the application program 847). Furthermore, the kernel 841 may provide an interface that allows the middleware 843, the API 845, or the application program 847 to access discrete components of the electronic device 801 so as to control or manage system resources.

The middleware 843 may perform a mediation role such that the API 845 or the application program 847 communicates with the kernel 841 to exchange data.

Furthermore, the middleware 843 may process task requests received from the application program 847 according to a priority. For example, the middleware 843 may assign the priority, which makes it possible to use a system resource (e.g., the bus 810, the processor 820, the memory 830, or the like) of the electronic device 801, to at least one of the application program 847. For example, the middleware 843 may process the one or more task requests according to the priority assigned to the at least one, which makes it possible to perform scheduling or load balancing on the one or more task requests.

The API 845 may be an interface through which the application program 847 controls a function provided by the kernel 841 or the middleware 843, and may include, for example, at least one interface or function (e.g., an instruction) for a file control, a window control, image processing, a character control, or the like.

The I/O interface 850 may transmit an instruction or data, input from a user or another external device, to other component(s) of the electronic device 801. Furthermore, the I/O interface 850 may output an instruction or data, received from other component(s) of the electronic device 801, to a user or another external device. For example, the input/output interface 850 may correspond to the module mounting structure 110 of FIGS. 1 and 3.

The display 860 may include, for example, a liquid crystal display (LCD), a light-emitting diode (LED) display, an organic LED (OLED) display, or a microelectromechanical systems (MEMS) display, or an electronic paper display. The display 860 may display, for example, various contents (e.g., a text, an image, a video, an icon, a symbol, and the like) to a user. The display 860 may include a touch screen and may receive, for example, a touch, gesture, proximity, or hovering input using an electronic pen or a portion of a user's body.

The communication interface 870 may establish communication between the electronic device 801 and an external electronic device (e.g., a first external electronic device 802, a second external electronic device 804, or a server 806). For example, the communication interface 870 may be connected to a network 862 through wireless communication or wired communication to communicate with an external device (e.g., the second external electronic device 804 or the server 806).

The wireless communication may include at least one of, for example, LTE (long-term evolution), LTE-A (LTE Advance), CDMA (Code Division Multiple Access), WCDMA (Wideband CDMA), UMTS (Universal Mobile Telecommunications System), WiBro (Wireless Broadband), or GSM (Global System for Mobile Communications), or the like, as cellular communication protocol. Furthermore, the wireless communication may include, for example, a local area network 864. The local area network 864 may include at least one of a wireless fidelity (Wi-Fi), a near field communication (NFC), or a global navigation satellite system (GNSS), or the like. The GNSS may include at least one of a global positioning system (GPS), a global navigation satellite system (Glonass), Beidou Navigation Satellite System (hereinafter referred to as "Beidou") or Galileo, the European global satellite-based navigation system, or the like. In this specification, "GPS" and "GNSS" may be interchangeably used. The wired communication may include at least one of, for example, a universal serial bus (USB), a high definition multimedia interface (HDMI), a recommended standard-232 (RS-232), or a plain old telephone service (POTS). The network 862 may include at least one of telecommunications networks, for example, a computer network (e.g., LAN or WAN), an Internet, or a telephone network.

Each of the first and second external electronic devices 802 and 804 may be a device of which the type is different from or the same as that of the electronic device 801 and/or the electronic device 100 of FIG. 3. According to an embodiment, the server 806 may include a group of one or more servers. According to various embodiments, all or a part of operations that the electronic device 801 will perform may be executed by another or a plurality of electronic devices (e.g., the electronic device 802 or 804, or the server 806). According to an embodiment, in the case where the electronic device 801 executes any function or service automatically or in response to a request, the electronic device 801 may not perform the function or the service internally, but, alternatively additionally, it may request at least a portion of a function associated with the electronic device 801 at other device (e.g., the electronic device 802 or 804 or the server 806). The other electronic device (e.g., the electronic device 802 or 804 or the server 806) may execute the requested function or additional function and may transmit the execution result to the electronic device 801. The electronic device 801 may provide the requested function or service using the received result or may additionally process the received result to provide the requested function or service. To this end, for example, cloud computing, distributed computing, or client-server computing may be used.

Figure 9:
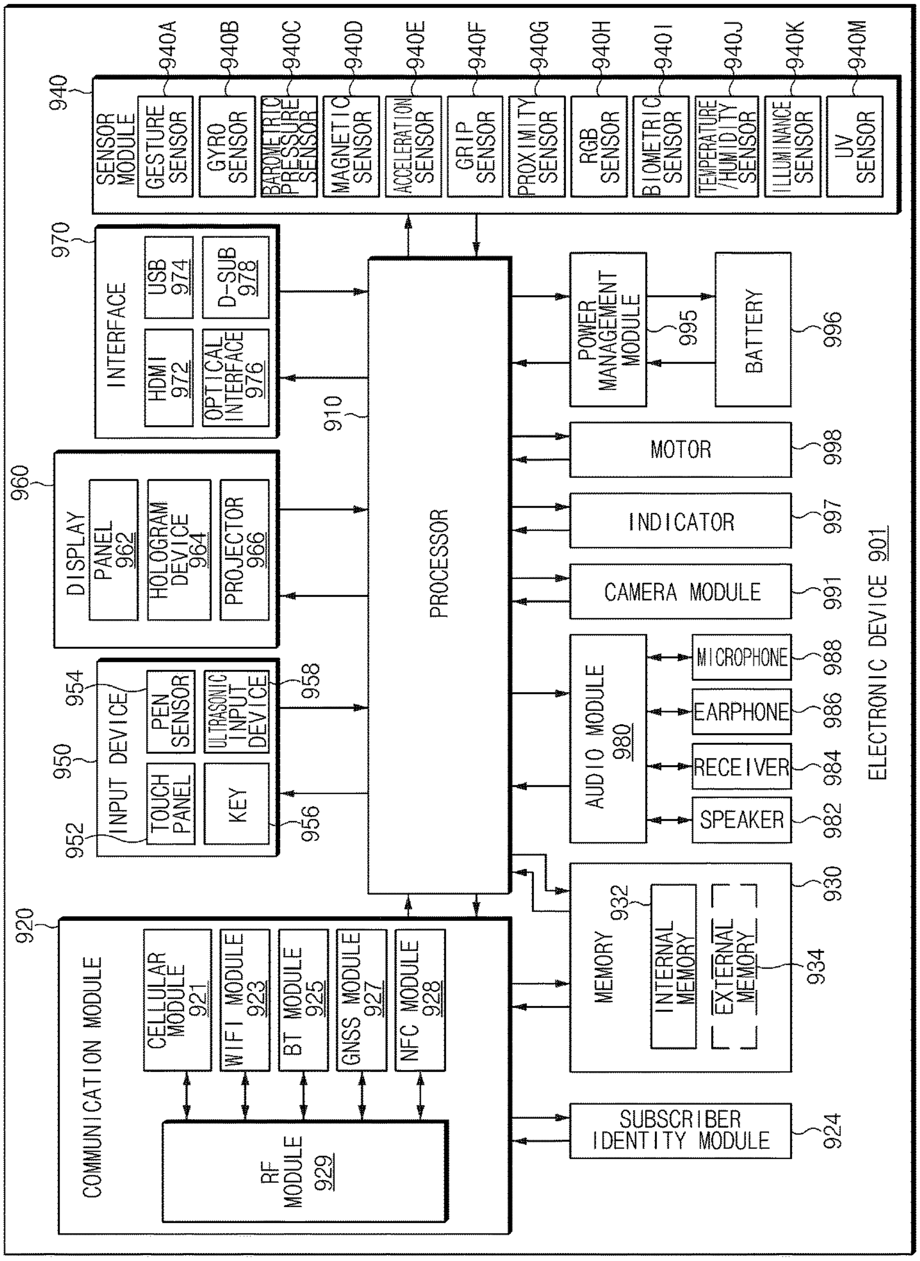
FIG. 9 is a block diagram illustrating an electronic device 901 according to various embodiments of the present disclosure.

FIG. 9 is a block diagram illustrating an electronic device 901 according to various embodiments of the present disclosure.

Referring now to FIG. 9, an electronic device 901 may include, for example, all or a part of the electronic device 100 illustrated in FIG. 3 and/or the electronic device 801 illustrated in FIG. 8. The electronic device 901 may include one or more processors (e.g., an application processor) 910, a communication module 920, a subscriber identity module 924, a non-transitory memory 930, a sensor module 940, an input device 950, a display 960, an interface 970, an audio module 980, a camera module 991, a power management module 995, a battery 996, an indicator 997, and a motor 998.

The one or more processors 910 may drive an operating system (OS) or an application program to control a plurality of hardware or software components connected to the one or more processors 910 and may process and compute a variety of data. The one or more processors 910 may be implemented with a System on Chip (SoC), for example. According to an embodiment, the one or more processors 910 may further include a graphic processing unit (GPU) and/or an image signal processor. The one or more processors 910 may include at least a part (e.g., a cellular module 921) of components illustrated in FIG. 9. The processor 910 may load and process an instruction or data, which is received from at least one of other components (e.g., a nonvolatile memory), and may store a variety of data at a nonvolatile memory.

The communication module 920 may be configured the same as or similar to the communication interface 870 of FIG. 8. The communication module 920 may include a cellular module 921, a Wi-Fi module 923, a Bluetooth (BT) module 925, a GNSS module 927 (e.g., a GPS module, a Glonass module, Beidou module, or a Galileo module), a near field communication (NFC) module 928, and a radio frequency (RF) module 929.

The cellular module 921 may provide voice communication, video communication, a character service, an Internet service or the like through a communication network. According to an embodiment, the cellular module 921 may perform discrimination and authentication of the electronic device 901 within a communication network using the subscriber identity module 924 (e.g., a SIM card), for example. According to an embodiment, the cellular module 921 may perform at least a portion of functions that the processor 910 provides. According to an embodiment, the cellular module 921 may include a communication processor (CP).

Each of the Wi-Fi module 923, the BT module 925, the GNSS module 927, and the NFC module 928 may include at least one processor for processing data exchanged through a corresponding module, for example. According to an embodiment, at least a portion (e.g., two or more components) of the cellular module 921, the Wi-Fi module 923, the BT module 925, the GNSS module 927, and the NFC module 928 may be included within one Integrated Circuit (IC) or an IC package.

The RF module 929 may transmit and receive, for example, a communication signal (e.g., an RF signal). The RF module 929 may include a transceiver, a power amplifier module (PAM), a frequency filter, a low noise amplifier (LNA), an antenna, or the like. According to various embodiments, at least one of the cellular module 921, the Wi-Fi module 923, the BT module 925, the GNSS module 927, or the NFC module 928 may transmit and receive an RF signal through a separate RF module.

The subscriber identity module 924 may include, for example, a card and/or embedded SIM that includes a subscriber identity module and may include unique identification information (e.g., integrated circuit card identifier (ICCID)) or subscriber information (e.g., international mobile subscriber identity (IMSI)). For example, the subscriber identity module 924 may correspond to the contact portion 201 of the module 200 illustrated in FIGS. 1 and 3 and may be coupled with the module housing 202 of the module 200.

The memory 930 (e.g., the memory 830 of FIG. 8) may include an internal memory 932 or an external memory 934. For example, the internal memory 932 may include at least one of a volatile memory (e.g., a dynamic random access memory (DRAM), a static RAM (SRAM), or a synchronous DRAM (SDRAM)), a nonvolatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a flash memory (e.g., a NAND flash memory, or a NOR flash memory), a hard drive, or a solid state drive (SSD).

The external memory 934 may include a flash drive, for example, compact flash (CF), secure digital (SD), micro secure digital (Micro-SD), mini secure digital (Mini-SD), extreme digital (xD), multimedia card (MMC), a memory stick, or the like. The external memory 934 may be functionally and/or physically connected to the electronic device 901 through various interfaces (e.g., the module mounting structure 110).

The sensor module 940 may measure, for example, a physical quantity or may detect an operation state of the electronic device 901. The sensor module 940 may convert the measured or detected information to an electric signal. The sensor module 940 may include at least one of a gesture sensor 940A, a gyro sensor 940B, a barometric pressure sensor 940C (e.g., the barometric pressure sensor 130 of FIG. 3), a magnetic sensor 940D, an acceleration sensor 940E, a grip sensor 940F, a proximity sensor 940G, a color sensor 940H (e.g., red, green, blue (RGB) sensor), a biometric sensor 940I, a temperature/humidity sensor 940J, an illuminance sensor 940K, or an UV sensor 940M. Even though not illustrated, additionally or alternatively, the sensor module 940 may further include, for example, an E-nose sensor, an electromyography sensor (EMG) sensor, an electroencephalogram (EEG) sensor, an electrocardiogram (ECG) sensor, an infrared (IR) sensor, an iris sensor, and/or a fingerprint sensor. The sensor module 940 may further include a control circuit for controlling at least one or more sensors included therein.

According to an embodiment of the present disclosure, the electronic device 901 may further include at least one processor (e.g., the first processor 141, a low-power processor, or a sensor module), which is a portion of the one or more processors 910 (e.g., the processor 140 of FIG. 4) or independent of the one or more processors 910, configured to control the sensor module 940 and may control the sensor module 940 while the processor 910 (e.g., the second processor 142 of FIG. 4) is in a sleep state.

The input device 950 may include, for example, a touch panel 952, a (digital) pen sensor 954, a key 956, or an ultrasonic input unit 958. The touch panel 952 may use at least one of capacitive, resistive, infrared and ultrasonic detecting methods. Also, the touch panel 952 may further include a control circuit. The touch panel 952 may further include a tactile layer to provide a tactile reaction to a user.

The (digital) pen sensor 954 may be, for example, a part of a touch panel or may include an additional sheet for recognition. The key 956 may include, for example, a physical button, an optical key, a keypad, and the like. The ultrasonic input device 958 may detect (or sense) an ultrasonic signal, which is generated from an input device, through a microphone (e.g., a microphone 988) and may check data corresponding to the detected ultrasonic signal.

The display 960 (e.g., the display 860 of FIG. 8) may include a panel 962, a hologram device 964, or a projector 966. The panel 962 may include a configuration which is the same as or similar to the display 150 of FIGS. 1 and 3 or the display 860 of FIG. 8. The panel 962 may be implemented to be flexible, transparent or wearable, for example. The panel 962 and the touch panel 952 may be integrated into a single module. The hologram device 964 may display a stereoscopic image in a space using a light interference phenomenon. The projector 966 may project light onto a screen so as to display an image. The screen may be arranged in the inside or the outside of the electronic device 901. According to an embodiment of the present disclosure, the display 960 may further include a control circuit for controlling the panel 962, the hologram device 964, or the projector 966.

The interface 970 may include, for example, the module mounting structure 110 of FIGS. 1 and 3. For example, the interface 970 may include an HDMI (high-definition multimedia interface) 972, a USB (universal serial bus) 974, an optical interface 976, or a D-sub (D-subminiature) 978. The interface 970 may be included, for example, in the communication interface 870 illustrated in FIG. 8. Additionally or alternatively, the interface 970 may include, for example, a mobile high definition link (MI-IL) interface, a SD card/multi-media card (MMC) interface, or an infrared data association (IrDA) standard interface.

The audio module 980 may convert a sound and an electric signal in dual directions. At least a portion of the audio module 980 may be included, for example, in the input/output interface 850 illustrated in FIG. 8. The audio module 980 may process, for example, sound information that is input or output through a speaker 982, a receiver 984, an earphone 986, or a microphone 988.

With continued reference to FIG. 9, the camera module 991 for shooting a still image or a video may include, for example, at least one image sensor (e.g., a front sensor or a rear sensor), a lens, an image signal processor (ISP), or a flash (e.g., an LED or a xenon lamp)

The power management module 995 may manage, for example, power of the electronic device 901. According to an embodiment of the present disclosure, a power management integrated circuit (PMIC) a charger IC, or a battery or fuel gauge may be included in the power management module 995. The PMIC may have a wired charging method and/or a wireless charging method. The wireless charging method may include, for example, a magnetic resonance method, a magnetic induction method or an electromagnetic method and may further include an additional circuit, for example, a coil loop, a resonant circuit, or a rectifier, and the like. The battery gauge may measure, for example, a remaining capacity of the battery 996 and a voltage, current or temperature thereof while the battery is charged. The battery 996 may include, for example, a rechargeable battery or a solar battery.

The indicator 997 may display a specific state of the electronic device 901 or a portion thereof (e.g., the one or more processors 910), such as a booting state, a message state, a charging state, or the like. The motor 998 may convert an electrical signal into a mechanical vibration and may generate the following effects such as: vibratory, haptic, and the like. Even though not illustrated, a processing device (e.g., a GPU) for supporting a mobile TV may be included in the electronic device 901. The processing device for supporting a mobile TV may process media data according to the standards of digital multimedia broadcasting (DMB), digital video broadcasting (DVB), MediaFlo™, or the like.

Each of the above-mentioned elements of the electronic device according to various embodiments of the present disclosure may be configured with one or more components, and the names of the elements may be changed according to the type of the electronic device. The electronic device according to various embodiments of the present disclosure may include at least one of the above-mentioned elements, and some elements may be omitted or other additional elements may be added. Furthermore, some of the elements of the electronic device according to various embodiments of the present disclosure may be combined with each other so as to form one entity, so that the functions of the elements may be performed in the same manner as before the combination.

Figure 10:
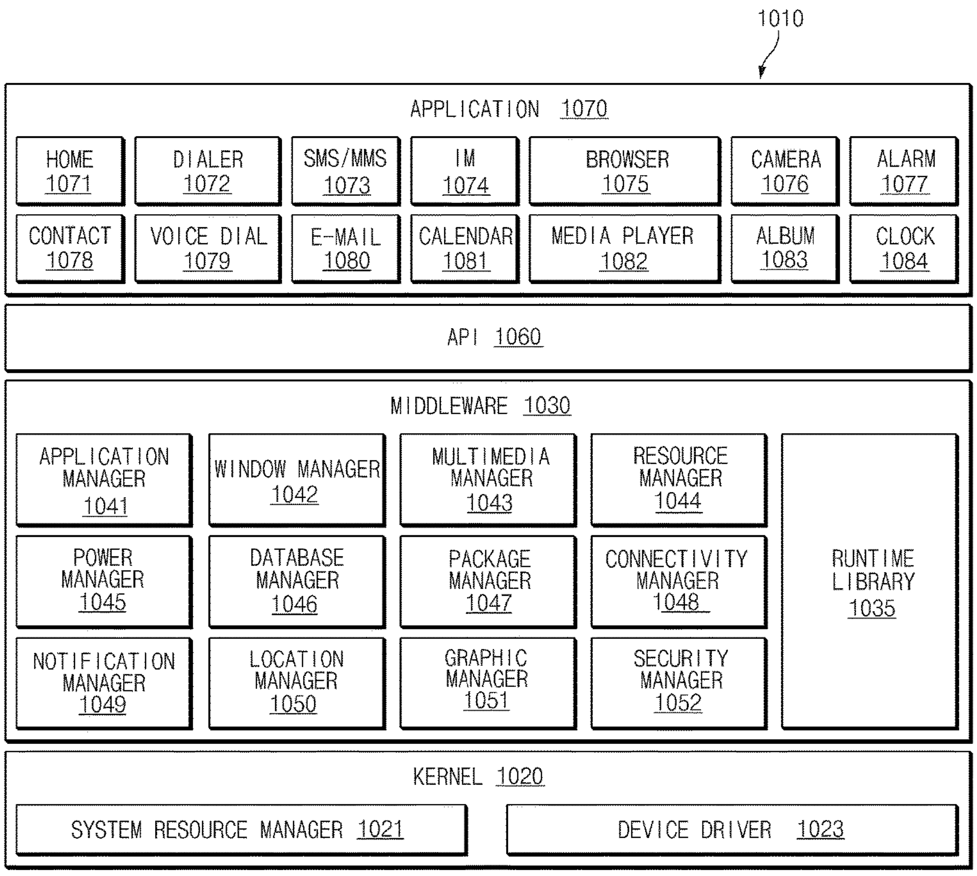
FIG. 10 illustrates a block diagram of a program module according to various embodiments of the present disclosure.

FIG. 10 illustrates a block diagram of a program module according to various embodiments of the present disclosure.

Referring now to FIG. 10, a program module 1010 (e.g., the program 840 of FIG. 8) may include an operating system (OS) to control resources associated with an electronic device (e.g., the electronic device 801 of FIG. 8), and/or diverse applications (e.g., the application program 847 of FIG. 8) driven on the OS. The OS may be, for example, Android, iOS, Windows, Symbian, Tizen, or Bada.

The program module 1010 may include a kernel 1020, a middleware 1030, an application programming interface (API) 1060, and/or an application 1070. At least a part of the program module 1010 may be preloaded on an electronic device or may be downloadable from an external electronic device (e.g., the electronic devices 802 and 804, the server 806, and the like of FIG. 8).

The kernel 1020 (e.g., the kernel 841 of FIG. 8) may include, for example, a system resource manager 1021 and/or a device driver 1023. The system resource manager 1021 may perform control, allocation, or retrieval of system resources. According to an embodiment of the present disclosure, the system resource manager 1021 may include a process managing part, a memory managing part, or a file system managing part. The device driver 1023 may include, for example, a display driver, a camera driver, a Bluetooth driver, a common memory driver, an USB driver, a keypad driver, a Wi-Fi driver, an audio driver, or an inter-process communication (IPC) driver.

The middleware 1030 may provide, for example, a function which the application 1070 needs in common, or may provide diverse functions to the application 1070 through the API 1060 to allow the application 1070 to efficiently use limited system resources of the electronic device. According to an embodiment, the middleware 1030 (e.g., the middleware 843 of FIG. 8) may include at least one of a runtime library 1035, an application manager 1041, a window manager 1042, a multimedia manager 1043, a resource manager 1044, a power manager 1045, a database manager 1046, a package manager 1047, a connectivity manager 1048, a notification manager 1049, a location manager 1050, a graphic manager 1051, or a security manager 1052.

The runtime library 1035 may include, for example, a library module which is used by a compiler to add a new function through a programming language while the application 1070 is being executed. The runtime library 1035 may perform input/output management, memory management, or capacities about arithmetic functions.

The application manager 1041 may manage, for example, a life cycle of at least one application of the application 1070. The window manager 1042 may manage a GUI resource which is used in a screen. The multimedia manager 1043 may identify a format necessary for playing diverse media files and may perform encoding or decoding of media files by using a codec suitable for the format. The resource manager 1044 may manage resources such as a storage space, memory, or source code of at least one application of the application 1070.

The power manager 1045 may operate, for example, with a basic input/output system (BIOS) to manage a battery or power and may provide power information for an operation of an electronic device. The database manager 1046 may generate, search for, or modify database which is to be used in at least one application of the application 1070. The package manager 1047 may install or update an application which is distributed in the form of package file.

The connectivity manager 1048 may manage, for example, wireless connection such as Wi-Fi or Bluetooth. The notification manager 1049 may display or notify an event such as arrival message, promise, or proximity notification in a mode that does not disturb a user. The location manager 1050 may manage location information of an electronic device. The graphic manager 1051 may manage a graphic effect that is provided to a user, or manage a user interface relevant thereto. The security manager 1052 may provide a general security function necessary for system security or user authentication. According to an embodiment of the present disclosure, in the case where an electronic device (e.g., the electronic device 801 of FIG. 8) includes a telephony function, the middleware 1030 may further includes a telephony manager for managing a voice or video call function of the electronic device.

The middleware 1030 may include a middleware module that combines diverse functions of the above-described components. The middleware 1030 may provide a module specialized to each OS kind to provide differentiated functions. Additionally, the middleware 1030 may remove a part of the preexisting components, dynamically, or may add a new component thereto.

The API 1060 (e.g., the API 845 of FIG. 8) may be, for example, a set of programming functions and may be provided with a configuration which is variable depending on an OS. For example, in the case where an OS is Android or the iOS, it may be permissible to provide one API set per platform. In the case where an OS is the Tizen, it may be permissible to provide two or more API sets per platform.

The application 1070 (e.g., the application program 847 of FIG. 8) may include, for example, one or more applications capable of providing functions for a home 1071, a dialer 1072, an SMS/MMS 1073, an instant message (IM) 1074, a browser 1075, a camera 1076, an alarm 1077, a contact 1078, a voice dial 1079, an e-mail 1080, a calendar 1081, a media player 1082, an album 1083, and a clock 1084, or for offering health care (e.g., measuring an exercise quantity or blood sugar) or environment information (e.g., atmospheric pressure, humidity, or temperature).

According to an embodiment of the present disclosure, the application 1070 may include an application (hereinafter referred to as "information exchanging application" for descriptive convenience) to support information exchange between the electronic device (e.g., the electronic device 801 of FIG. 8) and an external electronic device (e.g., the electronic device 802 or 804 of FIG. 8). The information exchanging application may include, for example, a notification relay application for transmitting specific information to the external electronic device, or a device management application for managing the external electronic device.

For example, the notification relay application may include a function of transmitting notification information, which arises from other applications (e.g., applications for SMS/MMS, e-mail, health care, or environmental information) of an electronic device, to an external electronic device (e.g., the electronic device 802 or 804 of FIG. 8). Additionally, the notification relay application may receive, for example, notification information from an external electronic device and provide the notification information to a user.

The device management application may manage (e.g., install, delete, or update), for example, at least one function (e.g., turn-on/turn-off of an external electronic device itself (or a part of components) or adjustment of brightness (or resolution) of a display) of the external electronic device (e.g., the electronic device 802 or 804 of FIG. 8) which communicates with the electronic device, an application running in the external electronic device, or a service (e.g., a call service, a message service, or the like) provided from the external electronic device.

According to an embodiment of the present disclosure, the application 1070 may include an application (e.g., a health care application of a mobile medical device, or the like) which is assigned in accordance with an attribute of the external electronic device (e.g., the electronic device 802 or 804 of FIG. 8). According to an embodiment, the application 1070 may include an application which is received from an external electronic device (e.g., the server 806 or the electronic device 802 or 804 of FIG. 8). According to an embodiment of the present disclosure, the application 1070 may include a preloaded application or a third party application which is downloadable from a server. The component titles of the program module 1010 according to an embodiment of the present disclosure may be modifiable depending on kinds of OSs.

According to various embodiments of the present disclosure, at least a portion of the program module 1010 may be implemented by software, firmware, hardware, or a combination of two or more thereof. At least a portion of the program module 1010 may be implemented (e.g., executed), for example, by at least one processor (e.g., the processor 910 of FIG. 9). At least a portion of the program module 1010 may include, for example, modules, programs, routines, sets of instructions, or processes, or the like for performing one or more functions.

At least a portion of an apparatus (e.g., modules or functions thereof) or a method (e.g., operations) according to various embodiments of the present disclosure may be, for example, implemented by instructions stored in a computer-readable storage media in the form of a program module. The instruction, when executed by a processor (e.g., the processor 820 of FIG. 8), may cause the one or more processors to perform a function corresponding to the instruction. The computer-readable storage media, for example, may be the memory 830 of FIG. 8.

The apparatuses and methods of the disclosure can be implemented in hardware, and in part as firmware or via the execution of software or computer code in conjunction with hardware that is stored on a non-transitory machine readable medium such as a CD ROM, a RAM, a floppy disk, a hard disk, or a magneto-optical disk, or computer code downloaded over a network originally stored on a remote recording medium or a non-transitory machine readable medium and stored on a local non-transitory recording medium for execution by hardware such as a processor, so that the methods described herein are loaded into hardware such as a general purpose computer, or a special processor or in programmable or dedicated hardware, such as an ASIC or FPGA. As would be understood in the art, the computer, the processor, microprocessor controller, control unit or the programmable hardware include memory components, e.g., RAM, ROM, Flash, etc., that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. In addition, an artisan understands and appreciates that a "processor", "microprocessor", "controller", or "control unit" constitute hardware in the claimed disclosure that contain circuitry that is configured for operation. Under the broadest reasonable interpretation, the appended claims constitute statutory subject matter in compliance with 35 U.S.C. § 101 and none of the elements are software per se. No claim element herein is to be construed under the provisions of 35 U.S.C. 112, sixth paragraph, unless the element is expressly recited using the phrase "means for".

The definition of the terms "unit" or "module" as referred to herein are to be understood as constituting hardware circuitry such as a CCD, CMOS, SoC, AISC, FPGA, a processor or microprocessor (a controller) configured for a certain desired functionality, or a communication module containing hardware such as transmitter, receiver or transceiver, or a non-transitory medium comprising machine executable code that is loaded into and executed by hardware for operation, in accordance with statutory subject matter under 35 U.S.C. § 101 and do not constitute software per se. For example, the image processor in the present disclosure, and any references to an input unit and/or an output unit both comprise hardware circuitry configured for operation.

A computer-readable recording medium may include a hard disk, a magnetic media, a floppy disk, a magnetic media (e.g., a magnetic tape), an optical media (e.g., a compact disc read only memory (CD-ROM) and a digital versatile disc (DVD), a magneto-optical media (e.g., a floptical disk), and hardware devices (e.g., a read only memory (ROM), a random access memory (RAM), or a flash memory). Also, a program instruction may include not only a mechanical code such as generated by a compiler but also a high-level language code executable on a computer using an interpreter. The above-mentioned hardware device may be configured to operate as one or more software modules to perform operations according to various embodiments of the present disclosure, and vice versa.

According to various embodiments of the present disclosure, since the electronic device determines whether the module is mounted in the module mounting structure based on the variation in the barometric pressure inside the electronic device due to the mounting of the module, the electronic device may determine whether the module is mounted even though the electronic device is under operation (e.g., in a power-on state).

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device, comprising:

a module mounting structure configured to house a subscriber identity module, a barometric pressure sensor disposed in the module mounting structure, and at least one processor disposed in the module mounting structure and electrically connected to the barometric pressure sensor, wherein the at least one processor is configured to:

detect air pressure inside the module mounting structure by using the barometric pressure sensor, determine whether the subscriber identity module is mounted in the module mounting structure, based on a variation in the detected air pressure, and authenticate the electronic device within a communication network using the mounted subscriber identity module.

2. The electronic device of claim 1, if the variation of air pressure detected by the barometric sensor is greater than or equal to a specific value, the at least one processor determines whether or not the module is mounted in the module mounting structure.

3. The electronic device of claim 1, wherein the at least one processor sends a module search signal to the module mounting structure, the module mounting structure sends a response signal corresponding to the module search signal to the at least one processor, and the at least one processor determines whether or not the module is mounted to the module mounting structure, based on whether the response signal is received from the module mounting structure.

4. The electronic device of claim 3, wherein if the response signal is received from the module mounting structure, the at least one processor determines that the module is mounted in the module mounting structure.

5. The electronic device of claim 3, wherein if the response signal is not received from the module mounting structure, the at least one processor determines that the module is not mounted in the module mounting structure.

6. The electronic device of claim 3, wherein if the response signal is not received from the module mounting structure during a specific period of time, the at least one processor is configured to re-send the module search signal to the module mounting structure, and wherein the number of times that the module search signal is sent is set in advance by the processor.

7. The electronic device of claim 1, wherein the at least one processor includes a first processor and a second processor, the first processor comprises a low-power processor configured to generate an interrupt, which requests the second processor to determine whether or not the module is mounted, when the variation of the detected air pressure is greater than or equal to a specific value, and wherein the low-power processor is configured to send the interrupt to the second processor.

8. The electronic device of claim 7, wherein if the interrupt is received, the second processor is configured to switch from a sleep state to an active state.

9. The electronic device of claim 7, wherein if receiving the interrupt, the second processor sends a module search signal to the module mounting structure, the module mounting structure sends a response signal corresponding to the module search signal to the second processor, and the second processor determines whether or not the module is mounted, based on whether the response signal is received from the module mounting structure.

10. The electronic device of claim 1, wherein the electronic device comprises a wearable device.

11. A module recognition method of an electronic device which comprises a module mounting structure, the method comprising:

detecting air pressure inside the electronic device;

determining whether a subscriber identity module is mounted or not in the module mounting structure, based on a variation in the detected air pressure, and authenticating the electronic device within a communication network using the mounted subscriber identity module.

12. The method of claim 11, wherein the determining comprises:

determining whether or not the module is mounted if the variation of the detected air pressure is greater than or equal to a specific value.

13. The method of claim 11, wherein the determining comprises:

sending a module search signal to the module mounting structure, and determining whether or not the subscriber identity module is mounted based on whether a response signal corresponding to the module search signal is received.

14. The method of claim 13, wherein the determining further comprises:

determining that the subscriber identity module is mounted in the module mounting structure, if the response signal is received.

15. The method of claim 13, wherein the determining further comprises:

determining that the subscriber identity module is not mounted in the module mounting structure, if the response signal is not received from the module mounting structure.

16. The method of claim 13, wherein the determining further comprises:

re-sending the module search signal to the module mounting structure, if the response signal is not received during a specific period of time, and wherein the number of times that the module search signal is sent is set in advance.

17. The method of claim 11, wherein the determining comprises:

generating an interrupt which requests a processor to determine whether the subscriber identity module is mounted or not, when the variation of the detected air pressure is greater than or equal to a specific value; and sending a module search signal to the module mounting structure, if the interrupt is generated, and determining whether or not the subscriber identity module is mounted, based on whether a response signal corresponding to the module search signal is received.

18. The method of claim 17, further comprising:

switching a state of the electronic device from a sleep state to an active state, if the interrupt is generated.

* * * * *